(12) United States Patent
Olson, Jr. et al.

(10) Patent No.: US 8,690,957 B2
(45) Date of Patent: Apr. 8, 2014

(54) BONE GRAFT COMPOSITION, METHOD AND IMPLANT

(75) Inventors: Stanley W Olson, Jr., Germantown, TN (US); Christopher M. Lyons, Hernando, MS (US); Jeffrey H Nycz, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 2362 days.

(21) Appl. No.: 11/313,188

(22) Filed: Dec. 21, 2005

(65) Prior Publication Data

US 2007/0142916 A1 Jun. 21, 2007

(51) Int. Cl.
*A61F 2/34* (2006.01)

(52) U.S. Cl.
USPC .......................................................... 623/22.21

(58) Field of Classification Search
USPC ........................................... 623/18.11–20.19
See application file for complete search history.

(56) References Cited

U.S. PATENT DOCUMENTS

| | | | |
|---|---|---|---|
| 3,157,524 A | 11/1964 | Artandi | |
| 3,520,402 A | 7/1970 | Nichols | |
| 4,193,813 A | 3/1980 | Chvapil | |
| 5,108,432 A * | 4/1992 | Gustavson | 623/23.54 |
| 5,629,191 A | 5/1997 | Cahn | |
| 5,676,700 A | 10/1997 | Black | |
| 5,766,176 A | 6/1998 | Duncan | |
| 5,830,493 A | 11/1998 | Yokota | |
| 5,866,113 A | 2/1999 | Hendriks | |
| 5,919,234 A | 7/1999 | Lemperle | |
| 5,997,895 A | 12/1999 | Narotam | |
| 6,037,519 A | 3/2000 | McKay | |
| 6,090,996 A | 7/2000 | Li | |
| 6,179,841 B1 | 1/2001 | Jackson | |
| 6,261,586 B1 | 7/2001 | McKay | |
| 6,280,473 B1 | 8/2001 | Lemperle et al. | |
| 6,328,765 B1 | 12/2001 | Hardwick | |
| 6,346,123 B1 | 2/2002 | McKay | |
| 6,383,519 B1 | 5/2002 | Sapieszko | |
| 6,391,059 B1 | 5/2002 | Lemperle et al. | |
| 6,409,764 B1 | 6/2002 | White | |
| 6,485,517 B1 | 11/2002 | Michelson | |
| 6,495,127 B1 | 12/2002 | Wallace | |
| 6,521,246 B2 | 2/2003 | Sapieszko | |

(Continued)

FOREIGN PATENT DOCUMENTS

| | | |
|---|---|---|
| DE | 34 44 780 A1 | 6/1986 |
| DE | 3444780 | * 12/1986 |
| WO | WO 2006031196 A | 3/2003 |

OTHER PUBLICATIONS

William F. McKay, Steven M. Peckham and James S. Marotta, The Science of rhBMP-2, Qualilty Medical Publishing, Inc., Chapt. 2, BMP Basics, pp. 23-40 (2006) (distributed Sep. 2005).

(Continued)

*Primary Examiner* — David Isabella
*Assistant Examiner* — Ann Schillinger
(74) *Attorney, Agent, or Firm* — Sorell Lenna & Schmidt LLP (57) ABSTRACT

A bone regenerative composition includes a resorbable osteoconductive matrix and a multiplicity of substantially rigid nanofibers dispersed within structure of the matrix to impart structural integrity with nanofiber ends projecting out of a surface of the matrix to provide differential load bearing surface bristles.

13 Claims, 4 Drawing Sheets

(56) References Cited

U.S. PATENT DOCUMENTS

| | | |
|---|---|---|
| 6,548,077 B1 | 4/2003 | Gunasekaran |
| 6,630,153 B2 | 10/2003 | Long |
| 6,652,532 B2 | 11/2003 | Bonutti |
| 6,656,214 B1 | 12/2003 | Fogarty |
| 6,712,851 B1 | 3/2004 | Lemperle et al. |
| 6,752,938 B2 | 6/2004 | Wang et al. |
| 6,786,910 B2 | 9/2004 | Cohen et al. |
| 6,858,431 B2 | 2/2005 | Hair |
| 6,867,247 B2 | 3/2005 | Williams |
| 6,884,775 B1 | 4/2005 | Tabin |
| 6,911,046 B2 | 6/2005 | Schulter |
| 6,913,626 B2 | 7/2005 | McGhan |
| 6,949,252 B2 | 9/2005 | Mizuno |
| 2001/0018614 A1 | 8/2001 | Bianchi |
| 2001/0051833 A1 | 12/2001 | Walter |
| 2002/0110541 A1 | 8/2002 | Petersen |
| 2002/0111692 A1 | 8/2002 | Ralph |
| 2003/0014120 A1 | 1/2003 | Carson |
| 2003/0059742 A1 | 3/2003 | Webster |
| 2003/0069718 A1 | 4/2003 | Hollister |
| 2003/0180344 A1 | 9/2003 | Wise |
| 2003/0203008 A1 | 10/2003 | Gunasekaran |
| 2004/0002558 A1* | 1/2004 | McKay ........................ 523/115 |
| 2004/0206448 A1 | 10/2004 | Dubrow |
| 2004/0243246 A1 | 12/2004 | Lyren |
| 2004/0247641 A1 | 12/2004 | Felt |
| 2005/0169893 A1 | 8/2005 | Koblish |
| 2005/0214341 A1 | 9/2005 | Brekke |
| 2005/0221072 A1 | 10/2005 | Dubrow |
| 2005/0228503 A1 | 10/2005 | Gundolf |

OTHER PUBLICATIONS

William F. McKay, Steven M. Peckham and James S. Marotta, The Science of rhBMP-2, Qualilty Medical Publishing, Inc., Chapt. 3, Overview of rhBMP-2, pp. 41-65 (2006) (distributed Sep. 2005).

William F. McKay, Steven M. Peckham and James S. Marotta, The Science of rhBMP-2, Qualilty Medical Publishing, Inc., Chapt. 4, rhBMP-2 and ACS, pp. 67-85 (2006) (distributed Sep. 2005).

Wong, Sheehan and Liebert, "Nanobeam Mechanics: Elasticity, Strength, and Toughness of Nanorods and Nanotubes," Science, 277, pp. 1971-1975 (Sep. 26, 1997).

Charulatha and Rajaram, "Influence of different crosslinking treatments on the physical properties of collagenmembranes," Biomaterials, 24, pp. 759-767 (Feb. 2003).

\* cited by examiner

BONE GRAFT COMPOSITION, METHOD AND IMPLANT

BACKGROUND OF THE INVENTION

The invention relates to a bone graft composition, method and implant for new tissue formation, including the surgical fixation of a joint to promote bone fusion. In an embodiment, the invention includes an absorbable matrix material in combination with an osteogenic composition.

A bone graft is a surgical procedure to place new bone into spaces around a broken bone or in between holes or defects in bone. The procedure can be used to repair broken bones that have bone loss, to repair injured bone that has not healed or to fuse joints to prevent movement. The bone graft procedure may be ancillary to an osteosynthesis, which is a surgical procedure that stabilizes and joins the ends of fractured bones by mechanical devices such as metal plates, pins, rods, wires or screws. The term "osteosynthesis" refers to internal fixation of a fracture by such means, as opposed to external fixation of a fracture by a splint or cast. Or, a bone graft may be part of a spinal fusion in which two or more of the vertebrae in the spine are united together so that motion no longer occurs between the vertebrae.

Modern bone grafting uses biologically active agents such as osteoinductive tissue growth factors to regenerate bone or cartilage. Bone morphogenetic proteins such as rhBMP-2, rhBMP-7 and rhBMP-12, are examples of osteoinductive tissue growth factors. Bone and articular cartilage regeneration with bone morphogenetic protein can be achieved through a tissue engineering approach based on bioresorbable synthetic osteoconductive scaffolds. These scaffolds are used to fabricate anatomically and functionally specific three dimensional tissue architecture. In some forms, the scaffolds provide a sponge matrix for the delivery of the biologically active agent and living cells to bone or cartilage defect.

Instructions for use of these materials suggest that compression of the biologically active agent within the osteoconductive media is undesirable. Compression or squeezing of the osteoconductive sponge matrix can result in migration of the beneficial biologically active therapeutic fluids away from treated anatomic structures. Also, compression, torsion or another force can cause the matrix to shift, extrude or rotate in placement.

There is a need for resorbable bone grafts with improved handling and compression resistance. There is a need for a bone graft implant that provides improved stability and mechanical strength and that resists shifting, extrusion and rotation after implantation.

BRIEF DESCRIPTION OF THE INVENTION

The invention relates to an improved bone regenerative composition that is compression resistant, provides improved stability and mechanical strength and resists shifting, extrusion and rotation after implantation.

In a first embodiment, the invention is a bone regenerative composition, comprising: a resorbable osteoconductive matrix; and a multiplicity of substantially rigid nanofibers dispersed within structure of the matrix to impart structural integrity and with nanofiber ends projecting out of a surface of the matrix to provide differential load bearing surface bristles.

Another embodiment of the invention is a method of producing a resorbable osteoconductive matrix, comprising: preparing a dispersion of collagen; dispersing nanofibers into the dispersion; and simultaneously drying and agitating the dispersion to provide a resorbable osteoconductive matrix with substantially rigid nanofibers dispersed within structure of the matrix to impart structural integrity and with nanofiber ends projecting out of a surface of the matrix to provide differential load bearing surface bristles.

Another embodiment of the invention is an implant, comprising: a resorbable osteoconductive matrix sheet formed in a shape for implanting into a tissue area in need of regeneration; and a supported interposed osteoinductive material; wherein the resorbable osteoconductive matrix sheet comprises substantially rigid nanofibers dispersed within structure of the matrix sheet to impart structural integrity and with nanofiber ends projecting out of a surface of the matrix sheet to provide a differential load bearing bristled surface above the matrix sheet surface.

In still another embodiment, the invention is a kit, comprising: an implant; and a resorbable osteoconductive matrix sheet formed in a shape for implanting with the implant into a tissue area in need of regeneration; and a supported interposed osteoinductive material; wherein the resorbable osteoconductive matrix sheet comprises substantially rigid nanofibers dispersed within structure of the matrix sheet to impart structural integrity and with nanofiber ends projecting out of a surface of the matrix sheet to provide a differential load bearing bristled surface above the matrix sheet surface.

And in another embodiment, the invention is a method for regenerating connective tissue, comprising administering an osteoinductive material to a site in need of tissue regeneration by inserting an implant within the site, wherein the implant comprises a structure with a bone regenerative composition comprising: a resorbable osteoconductive matrix; and a supported interposed osteoinductive material; wherein the resorbable osteoconductive matrix comprises a multiplicity of substantially rigid nanofibers dispersed within structure of the matrix to impart structural integrity and with nanofiber ends projecting out of a surface of the matrix to provide differential load bearing surface bristles.

DETAILED DESCRIPTION OF THE INVENTION

The invention provides a biocompatible composition for new bone formation. The composition includes a matrix for controlled delivery of bone growth inductive factors, such as bone morphogenetic protein (BMP). The composition of the invention is a biocompatible graft material with exceptional osteoconductive properties. The material can be pre-sized in a variety of forms, including strips and cylinders for restoring defects in bone; to provide bone graft materials that can be shaped; and to provide bone graft materials with improved handling properties. The graft material can be cut while dry or after being wetted and does not crumble.

The bone graft composition of the invention is at least partially load bearing and has improved pliability. The composition retains a high degree of porosity over a broad pore size distribution to maintain superior resorbtion, bone ingrowth properties and retention properties even under compressive loads. The composition is strong and compliant and conforms to adjacent surfaces. The composition has a bristled surface that resists shifting, extrusion and rotation after implantation.

Resorable Osteoconductive Matrix (ACS)

While type I collagen is a preferred source for the inventive resorbable osteoconductive matrix due to its availability, ease of isolation and purification, and biocompatible properties, other fibril forming collagen such as types II, III, V and XI and physiologically compatible collagen obtained from transgenic animals may be used either singularly or in combination with type I collagen. The primary source of type I collagen is tendon, skin, bone, and ligament. Human or animal tissues may be used to isolate the collagen. In general, animal tissues are preferred due to easy availability in fresh forms from local slaughter houses.

Advantageously, animal type I collagen is homologous to human type I collagen. Therefore, medical devices prepared from animal-derived (e.g., bovine, porcine, ovine, equine) type I collagen are accepted for human implantation. Type I collagen-based implants can enhance wound healing during tissue and organ regeneration. Type I collagen fibers can be engineered into a variety types of matrices. Cells and bioactive agents (drugs, growth factors, genes) can be incorporated for enhanced function. A final advantage is that Type I collagen-based products can be cost effectively manufactured in large quantities.

In a preferred embodiment, the osteoconductive matrix is purified from Type I bovine tendon collagen in the form of an absorbable collagen sponge (ACS). The purified type I collagen ACS material can be engineered into a variety of extracellular tissue matrices having specific characteristics to be used either alone or in combination with cells and bioactive molecules for tissue and organ regeneration applications.

ACS is derived from the Achilles tendon of steers at the beginning of beef production. The tendon is harvested in the United States from USDA-cleared food-grade herds. The tendon tissue is virtually avascular and is the first tissue to be harvested, which reduces the risk of infection or contamination. After harvesting, the tendon is treated with alkali solutions to become the sponge like material that is particularly suitable as the resorbable osteoconductive matrix of the invention. After the collagen is formed into a sponge, the material is sterilized with ethylene oxide.

ACS is available as an absorbable hemostatic agent, Helistat® agent from Integra Life Sciences, Plainsboro, N.J.). Once implanted, the ACS osteoconductive matrix undergoes resorbtion over a 4- to 12-week period via cell-mediated degradation by macrophages. The collagen can provide a favorable surface for cell attachment during early osteoid formation. It then undergoes resorbtion. ACS osteoconductive matrix possesses all the properties of an ideal carrier for many biological agents and is particularly suited for BMP.

The resorbable osteoconductive matrix of the invention has pores of a sufficient size and quantity to permit growing tissue to infiltrate therein. The pore size preferably ranges from about 10 μm to about 500 μm, more preferably from about 50 μm to about 150 μm with surface pores being smaller than cross-sectional (internal) pores. In particularly preferred embodiments, the surface pores range in diameter from about 30 μm to about 150 μm, with about 70 μm being most preferred. Cross-sectional pores can range in diameter from about 50 μm to about 300 μm, with about 150 μm being most preferred.

A film according to the invention can be provided by casting a dispersion of collagen having a collagen concentration of about 0.1 to about 10% solids (w:v) and, optionally, about 0.005 to 0.5% (w:w on collagen solids) of a suitable biocompatible plasticizer, such as glycerin. Preferably, the plasticizer concentration is about 0.1% and the collagen concentration is about 1%, more preferably 0.75%. A volume of the dispersion is poured into a suitable non-stick container and evaporated to provide a film having a thickness of about 0.05 to about 2.0 mm, preferably about 0.5 mm. The film can be cross-linked with heat or a suitable chemical cross-linking agent.

The film is prepared with nanofibers to provide a bristled surface that can provide a fitting to an underlying or overlying complementary bristled surface. The intermeshing bristle connection provides a secure fit between surfaces without complicated and expensive other mechanical attachments like compression fit structures or chemical attachments like adhesives or cements. Additionally, the bristled surfaces resist shifting, extrusion and rotation after implantation.

A preferred form of the resorbable osteoconductive matrix is describable as an homogeneous biologically compatible porous matrix having a isopycnic density with a liquid growth medium, a sponge-like character and diameters of less than about 2 millimeters, each particle having a multiplicity of voids, the voids representing at least 10 percent of the total volume of the matrix, the voids being connected to pores of less than 100 micrometers in diameter, which connect the voids to the exterior of the matrix.

A multicellular matrix sheet is another preferred form of the inventive resorbable osteoconductive matrix. In accordance with the invention, the multicellular matrix sheet is formed from a collagen dispersion with dispersed nanofiber.

Substantially Rigid Nanofibers

In this application, the term "substantially rigid" means substantially devoid of flexibility in the environment used. Rigidity can be measured by the modulus of elasticity in shear. In this aspect, "substantially rigid" can mean a nanofiber with a modulus of elasticity between 4.2 MPa and 15.0 MPa, desirably between 6.0 MPa and 14.0 MPa and preferably between 9.0 MPa and 12.0 MPa, with the higher MPa values obtainable by cross-linking The term "nanofiber" means an elongated nanostructure having one principal axis that is longer than the other two principal axes and an aspect ratio greater than one or greater than 10 or greater than 500. A shorter axis can be less than 100 nm, or less than 10 nm or less than 5 nm. The nanofiber can have a substantially uniform diameter. The diameter can show a variance less than 20%, less than 5%, or less than 1% over the region of greatest variability. Typically the diameter is evaluated away from the ends of the nanofiber over a central 20%, 50% or 80% of the nanofiber. In other embodiments, the nanofiber has a non-uniform diameter, varying in diameter along length. Also in certain embodiments, the nanofiber can be substantially crystalline and/or substantially monocrystalline.

"Nanofiber" includes such structures as nanowires, nanowhiskers, semi-conducting nanofibers, carbon nanotubes and composite nanotubes so long as they impart a bristled surface to the resorbable osteoconductive matrix of the invention. The nanofiber can comprise any number of materials, based on certain factors, including intended use of the bristled surface, conditions of use such as temperature, pH, light such as UV sensitivity, placement environment, reactions to be supported by the resorbable osteoconductive matrix, required surface durability and even cost. Ductility and breaking strength of the nanofibers can vary depending on composition. For example, ceramic ZnO nanofiber wires can be more brittle than silicon or glass nanowires, while carbon nanofiber tubes may have a higher tensile strength.

Although collagen is a good example of a rigid nanofiber, other polymers are suitable as well. Derivatives of other biopolymers that are rod-like, such as tubulin and keratin that can be manufactured in rigid nanofiber form can be suitable so long as they retain a fiber structure integrity under conditions of matrix formation. A preferred nanofiber is a nanometer scale rod-like polymer that is water compatible and has polar surface groups such as amino groups.

Other nanofibers for applications of the resorbable osteoconductive matrix include silicon, ZnO, TiO, carbon, carbon nanotubes, glass, and quartz. The nanofibers of the invention can be coated or functionalized to enhance or add properties. Polymers, ceramics or small molecules can be used as coating materials. The coatings can impart characteristics such as water resistance, improved mechanical or electrical properties or specificities for certain analytes. Additionally, specific moieties or functional groups can be attached to or associated with the nanofibers.

In an embodiment, the nanofiber is formed by methylated collagen. This material has a relatively high (above 25° C.) glass transition temperature that imparts improved structural integrity and surface bristling to the resorbable osteoconductive matrix.

Different applications of the invention will require different densities of nanofibers per unit volume of osteoconductive matrix. In some exemplary applications, the number of nanofibers per unit volume is 1 nanofiber per 10 micron$^3$ to 200 nanofibers per micro3 volume matrix or from 10 nanofibers per micron$^3$ to 100 nanofibers per micron$^3$; or from 25 nanofibers per micron$^3$ to 75 nanofibers per micron$^3$ volume matrix. In other nanowire embodiments, a density can range from about 1 to 3 nanowires per cubic micron to 2,500 nanowires per cubic micron of matrix.

An overall area of a nanofiber can be increased by increasing thickness or diameter. The diameter can be controlled through choice of composition, growth conditions, moieties or coatings. A preferred nanofiber thickness is between 5 nm to 1 micron; from 10 nm to 750 nanometers or from 75 nm to 100 nanometers.

In addition to diameter, surface area of nanofibers and correspondingly the bristled surface area of resorbable osteoconductive matrix are influenced by length of the nanofibers. For some fiber materials, increasing length results in increasing fragility. Accordingly, preferred fiber lengths will be between 2 microns and 1 mm; between 10 microns to 500 micrometers; or between 50 microns to 100 microns. Some embodiments of the invention have nanofibers of approximately 40 nm in diameter and approximately 50 microns in length.

The nanofibers can be substantially homogeneous in material properties or they can be heterogeneous. They can be fabricated from any convenient material or materials. The nanofibers can comprise "pure" materials, substantially pure materials and doped materials. They can include insulators, conductors or semiconductors. The nanofiber material can vary depending upon specific functionalization such as durability, cost or condition of use. The nanofiber material can be the same as the resorbable osteoconductive matrix material or the nanofiber material can be different from the matrix.

Producing the Matrix with Dispersed Nanofiber

The resorbable osteoconductive matrix comprises dispersed fibers, some of which have ends that are elevated above the matrix surface in a bristled pattern. In one embodiment, the matrix has least a portion of dispersed nanofibers that have ends that are elevated at least 10 nm, and in other embodiments at least 100 nm above the matrix surface. A preferred bone regenerative composition comprises bristled nanofiber ends extending between 40 nm and 100 nm above an ACS surface. The bristles form a complex brush-like texture that differentially supports adjacent structures to protect the cellular structure of the resorbable osteoconductive matrix from osteoinductive material loss from compression. Additionally, the brush like texture can provide a frictioned surface that resists slippage against adjacent surfaces and that securely fits to adjacent surfaces.

In a preferred method of making the nanofiber-containing matrix, nanofibers are dispersed in a collagen dispersion, which is then dried while agitated to a thin matrix or sheet. The collagen dispersion can be derived by any known process. For example, U.S. Pat. Nos. 3,157,524, and 3,520,402 disclose collagen dispersion preparations. These references disclose forming tendon collagen slices in an acid solution to form a dispersion that is then extruded into a coagulating bath. In particular, the collagen dispersion can be prepared according to the disclosure of Narotam U.S. Pat. No. 5,997,895, assigned to Integra Lifesciences Corporation. The disclosure of Narotam U.S. Pat. No. 5,997,895 is incorporated herein by reference in its entirety.

In the Narotam U.S. Pat. No. 5,997,895 procedure, a native source of Type I collagen, such as skin, tendon, ligament or bone, is first mechanically or hand cleaned of fat, fascia and other extraneous matter and washed. The cleaned and washed collagen containing material is then comminuted, generally by slicing or grinding. The material is then subjected to an enzyme treatment while under intermittent stirring with a proteolytic enzyme, such as ficin or pepsin so as to remove non-collagenous impurities that could cause antigenic activity. The enzyme treatment also swells the collagen by removing elastin. The amount of enzyme added to the collagen material and the conditions under which enzyme digestion takes place is dependent upon the particular enzyme used. Generally, when using ficin, which is commonly used, the pH is adjusted to about 6.0 to 6.3, and the collagen material is digested for about 1 to 2 hours at a temperature of about 36.5° C. to 37.5° C. with one part ficin for 150 parts of collagen material. After a requisite amount of time, the enzyme is inactivated, for example by adding a solution of an oxidizing agent, such as sodium chlorite (when the enzyme is ficin).

The enzyme treated collagen containing material is washed to remove excess enzyme and non-collagenous protein impurities. Preferably, the washing is carried out with ultrafiltered and deionized water. The collagen may be further washed with dilute aqueous hydrogen peroxide.

The enzyme digested collagen containing material can then be subjected to an alkali treatment at a pH of about 13 to 14, at a temperature of about 25° C. to 30° C. for a period of about 35 to 48 hours, preferably about 40 hours. The alkali treatment can be carried out in an aqueous solution of 5% sodium hydroxide and 20% sodium sulfate. Alkali treatment removes contaminating glycoproteins and lipids. The solution is then neutralized with a suitable acid, such as aqueous sulfuric acid, and thoroughly washed.

The collagen material is then further swollen with a suitable acid solution that does not cause cross-linking of the collagen. Suitable acids include acetic acid, hydrochloric acid and lactic acid. The acid is used to adjust the pH of the acid collagen dispersion to about 2 to 3.

The dispersed collagen mixture is then homogenized, for example in a blender or homogenizer, so as to further disassociate the fibers. The mixture is then filtered to remove unswollen, non-collagenous material; for example, by passing the dispersion through a 100 mesh stainless steel screen.

The nanofibers of the invention are added to the strained dispersion in a weight percent calculated on a number of nanofibers per unit volume of matrix, preferably per unit volume of ACS. For example, a weight percent added nanofiber can be calculated to provide 1 nanofiber per 10 micron$^3$ to 200 nanofibers per micro$^3$ of ACS volume. Then the ACS with nanofiber dispersion is poured into a suitable tray. The dispersion is frozen and lyophilized while agitated for about 1 to about 48 hours.

Mechanical agitation of the solidifying dispersion assures a random orientation of nanofibers so that at least a portion of nanofiber ends protrude from a surface of a solidified ACS matrix surface. The agitation can be applied uniformly to provide uniformly bristled surfaces. Or, the agitation can be selectively appliled to produce selected bristled surfaces. The agitation can be applied for example, by low-frequency sonication or by rocking the tray or stirring the solidifying dispersion. In one example, agitation is applied by ultrasonic vibration at a frequency between 2 kHz to less than 20 kHz, or at a frequency between 3 kHz to 10 kHz, preferably at a frequency between 4 kHz to 8 kHz. The agitation is applied until the dispersion has sufficiently solidified to support at least some of the nanofibers in an orientation that projects ends through matrix surface to form the invention bristled surface. The protrusion of bristled ends above the ACS surface can be non-uniform between 1 nm to 1000 nm or between 10 nm to 500 nm or 100 nm to 300 nm. Protrusion of any degree of the length of the bristles provides improved load bearing tensile strength compared to surface attached nanofibers. The protrusion can be defined as at least 0.1% average length to 99% average length beyond the matrix surface, desirably from 1% to 90% and preferably 10% to less than 50% average length protrusion of nanofibers beyond the matrix surface.

The resulting bristled sponge can have a thickness from 2.0 mm to 6 mm, preferably about 3 mm. The density of the nanofiber-containing dispersion and the lypophilization cycle dictate the sponge density and pore size. The bristled ACS has pores of a sufficient size and quantity to permit infiltration of growing tissue. The pore size can range from 10 μm to 500 μm, preferably from 50 μm to 150 μm, with surface pores being smaller than cross-sectional (internal) pores.

A film according to the invention can be provided by casting a dispersion of the nanofiber containing collagen having a collagen concentration of 0.1 to 10% solids (w:v) and 0.005 to 0.5% (w:w on collagen solids) of a suitable biocompatible plasticizer, such as glycerin. The plasticizer concentration can be about 0.1% and the collagen concentration about 1%, preferably 0.75% and the nanofiber concentration can be from 0.01% to 50%, desirably 0.1% to 10% and preferably 1% to 5%. A volume of the dispersion is poured into a suitable non-stick container and evaporated to provide a film having a thickness of 0.05 to 2.0 mm, preferably about 0.5 mm. The film can be cross-linked with heat or a suitable chemical cross-linking agent.

In another method, a collagen sponge or film is cast from lactic acid derived collagen fibers containing the nanofibers. The collagen fibers are produced by a process comprising dispersing a virus and prion free collagen source such as alkali-treated bovine tendon slices, in an aqueous solution of lactic acid, homogenizing the dispersion, filtering the homogenized lactic acid dispersion, and precipitating collagen fibers from the homogenized lactic acid dispersion by addition of aqueous ammonium hydroxide sufficient to adjust the pH to about 4.6-4.9.

An ACS and film laminate can be prepared by casting a collagen film; drying the film; casting a nanofiber-containing collagen slurry onto the dried film; lyophilizing the slurry/film combination; and cross-linking the lyophilized laminate product by exposing it to vapors from an aqueous formaldehyde solution (preferably having a 9.6% formaldehyde concentration) for about ninety minutes at about 25° C., followed by forced air ventilation for about one hour.

Biological Agent (Bone Morphogenetic Protein (BMP))

The term "biological agent" defines an entity that is added to the osteoconductive matrix to effect a therapeutic end, such as facilitation of bone growth, prevention of disease, administration of pain relief chemicals, administration of drugs, and the like. Examples of biological agents include antibiotics, growth factors, fibrin, bone morphogenetic factors including bone morphogenetic protein (BMP), bone growth agents, chemotherapeutics, pain killers, bisphosphonates, strontium salt, fluoride salt, magnesium salt and sodium salt.

Preferred biological agents include bone morphogenetic proteins (BMPs) that belong to the transforming growth factor-{3 (TGF.(3) superfamily of structurally related signaling proteins. They initiate, promote and regulate bone development, growth, remodeling and repair. In addition to bone and cartilage morphogenesis, BMP is involved in prenatal development and postnatal growth of eye, heart, lung, kidney, skin and other tissues. Many BMPs have osteoinductive capability since they induce mesenchymal stem cells into osteoblasts, the cells that form new bone. Studies have demonstrated the efficacy of some BMPs in bone repair. Specific to the spine, studies have shown comparable or improved spine fusion rates with use of BMP in a carrier versus use of an autograft.

Features of the invention will become apparent from the drawings and following detailed discussion, which by way of example without limitation describe preferred embodiments of the invention.

Figure 1:
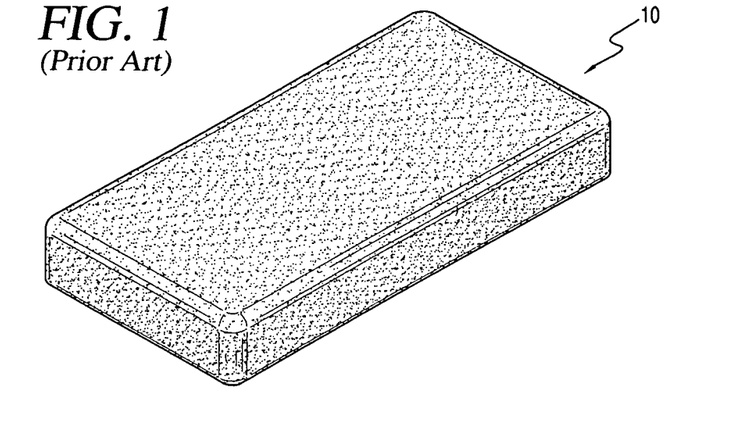
FIG. 1 is a schematic, disproportionate perspective view of a prior art resorbable osteoconductive matrix.
Figure 2:
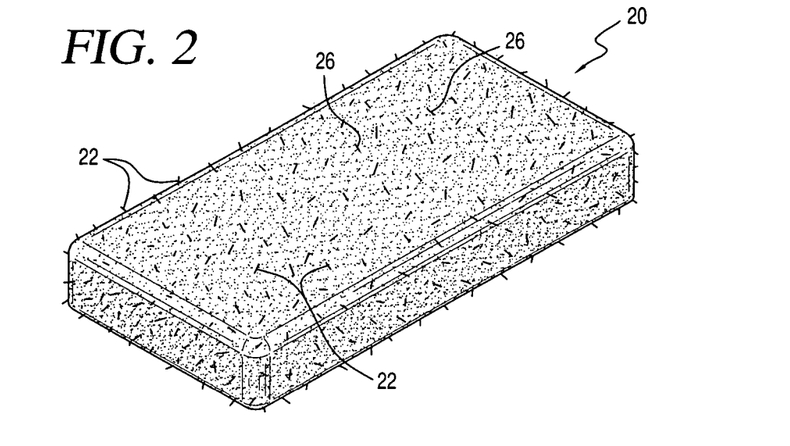
FIG. 2 is a schematic, disproportionate perspective view of a bristled resorbable osteoconddctive matrix.
Figure 3:
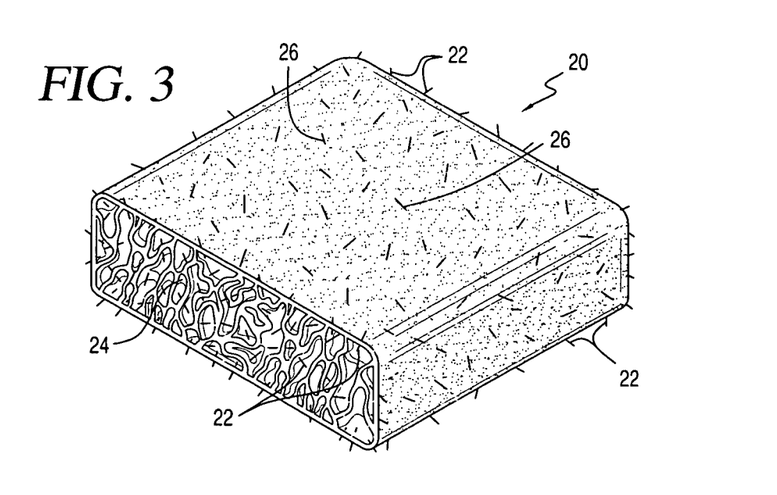
FIG. 3 is a cut away view of the FIG. 2 matrix.

FIG. 1, FIG. 2 and FIG. 3 are schematic, disproportionate perspective views of resorbable osteoconductive matrices. In each view, at least a height dimension is substantially exaggerated to show a height bristled dimension and a cellular and dispersed nanofiber interior structure. FIG. 1 represents a prior art matrix 10. FIG. 2 represents a resorbable osteoconductive matrix according to the invention with bristles surfaces. FIG. 3 shows disperse red bristles 22 throughout the interior cellular pore structure 24. Both FIG. 2 and FIG. 3 show the resorbable osteoconductive matrix structure 20 with bristle ends 26 outstanding from each surface. These bristles impart an improved intrastructural stability and mechanical strength to the resorbable osteoconductive matrix structure 20, while outstanding bristle ends provide differential load bearing structures and a surface that resists shifting and rotation, as hereinafter described with reference to FIGS. 4, 5 and 6.

Figures 4, 5, 6:
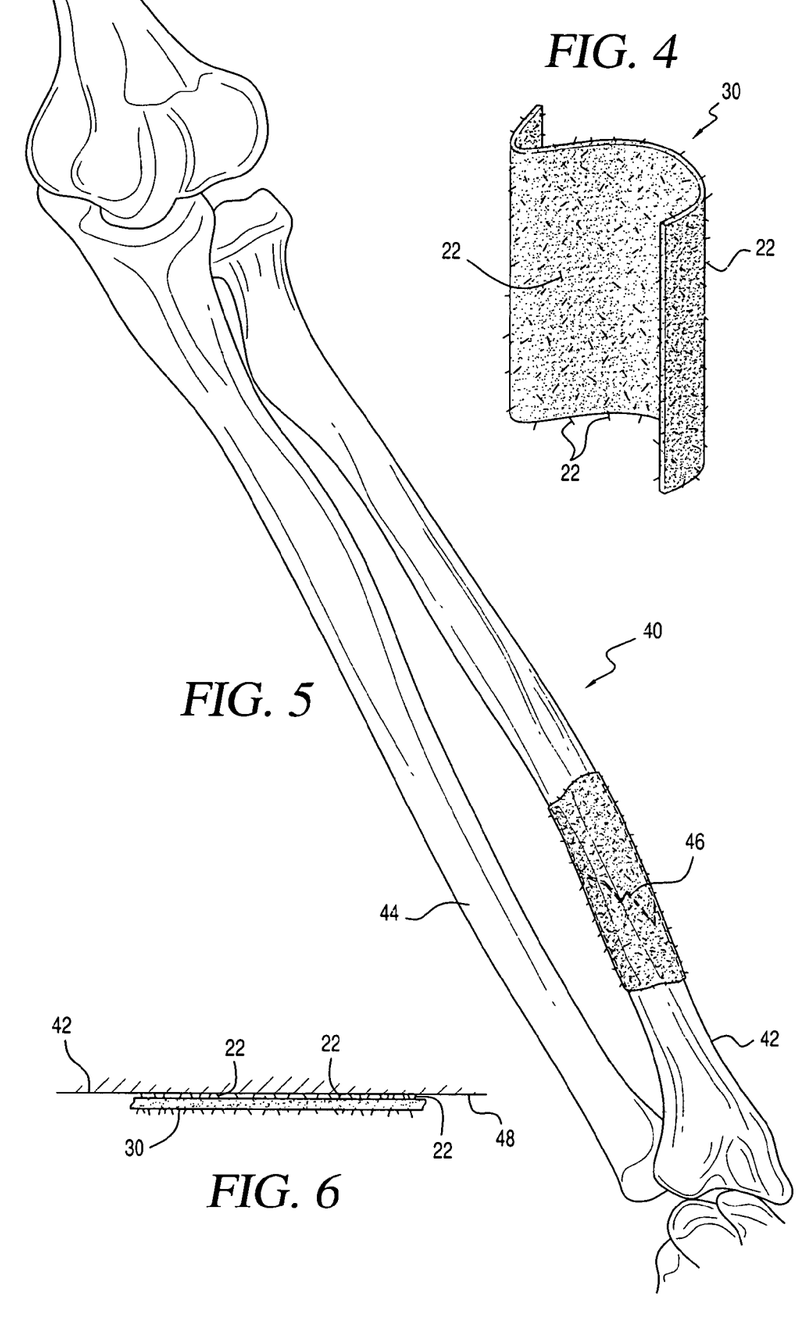
FIG. 4 illustrates a sheet form of a resorbable osteoconductive matrix with bristled surfaces.
FIG. 5 is a schematic representation of a resorbable osteoconductive matrix in sheet form applied as a protective bone regeneration to a long bone defect.
FIG. 6 is a schematic side view of the application of a matrix sheet form 30 to an ulna surface.

FIG. 4 shows a sheet form 30 of the resorbable osteoconductive matrix with bristled 22 surface. The form is rollable and foldable and is particularly useful in applications such as shown in FIG. 5. FIG. 5 illustrates the protective bone regeneration matrix sheet form 30 of the present invention, as applied to a patient's arm 40 long bone defect. FIG. 5 shows radius 42 and ulna 44. Radius 42 has fracture 46. The resorbable osteoconductive matrix sheet form 30 is tightly wrapped around the radius 42 at the location of the fracture 46. The tight wrap assures firm placement of the sheet form 30 and sorbed biological agent. FIG. 6 illustrates the application of the matrix sheet form 30 to ulna 42 surface 48. FIG. 6 shows ends of bristles 22 biased against the surface 48 to differentially bear the load against the ulna surface 48 imposed by the tight wrapping of sheet 30. Conventional matrices cannot be tightly wrapped because resulting surface compression will squeeze active sorbed biological agent from the matrix before the agent can effect a therapeutic result. With the invention, surface compression is differentially bom by the bristles 22 and sorbed biological agent is lost only in the immediate area of the bristle if at all.

Figures 7, 8:
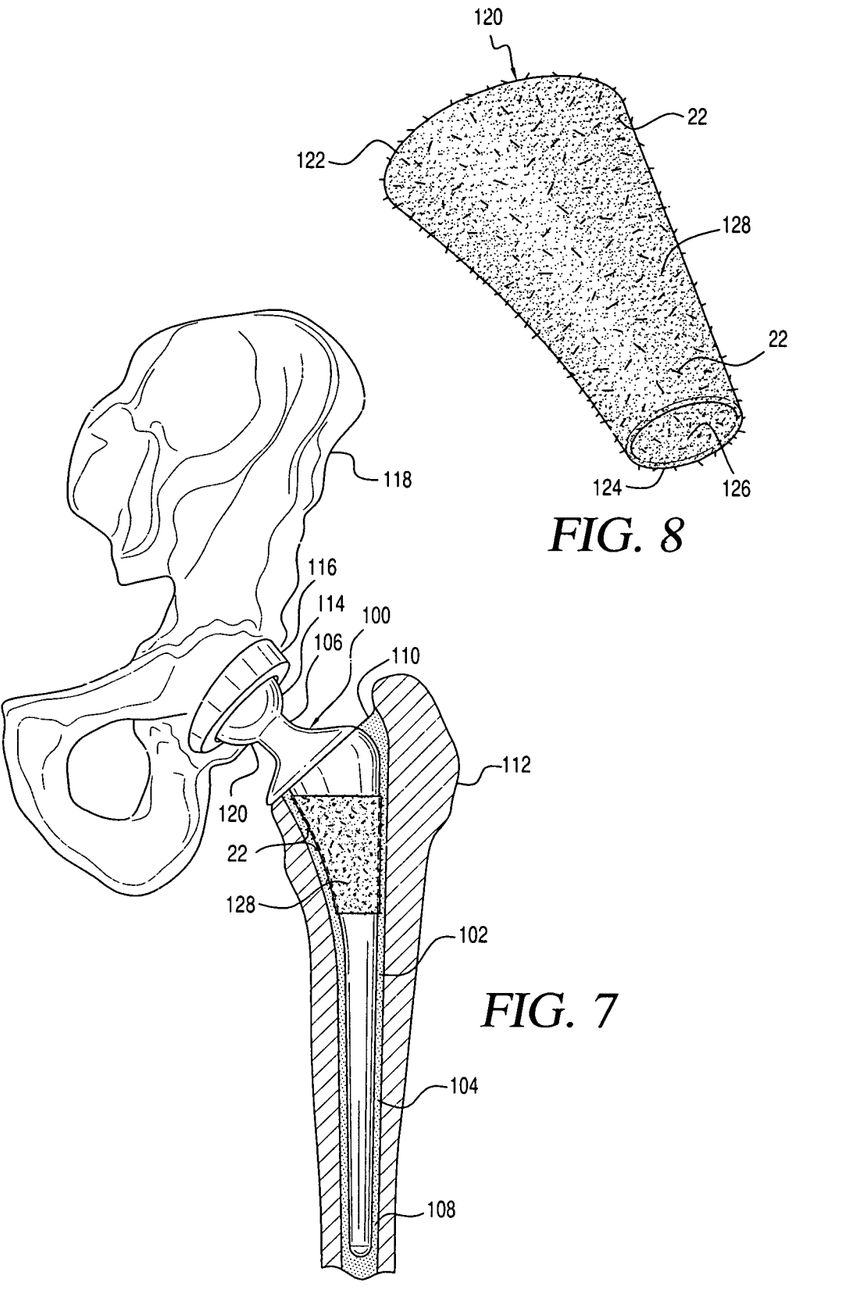
FIG. 7 is a schematic perspective view of a hip implant.
FIG. 8 is a schematic perspective view of a seating element used in conjunction with the FIG. 7 hip implant.

FIG. 7 shows a hip implant 100 including a femoral stem 102, which includes a shaft portion 104 having a proximal end 106 and a distal end 108, the distal end 108 being shaped for insertion into the axial bore 110 of a patient's femur 112. This stem 102 further includes, at its proximal end 106, a ball-shaped surface 114 for insertion into a receiving cup 116 disposed in an acetabular recess in the patient's pelvis 118. The stem 102 comprises the shaft portion 104 and a ball-shaped head 114 disposed at the proximal end 106 of the shaft 104.

Seating element 120 is shown in enlarged detail in FIG. 8. Seating element 120 comprises a sheet bone regenerative composition formed as a frusto-conical tubular member having a proximal 122 and a distal 124 end. Dispersed bristles 22 provide an interior bristle surface 126 and an exterior bristle surface 128. The seating element 120 is tapered such that it narrows in the direction of the distal end 124 to conform to the shape of the shaft portion 104 of femoral stem 102.

As shown in FIG. 7, the femoral stem 102 of the implant 100 is inserted within the seating element 120 prior to insertion of the implant 100 into the patient's femur 112. When the implant 100 is inserted, the seating element 120 is compression fit into the axial bore 110 of the patient femur 112 with the bristles 22 of the exterior surface 128 providing load bearing against adjacent femur 112 and the bristles 22 of the interior surface 126 providing load bearing against the adjacent implant 100. Additionally, the bristle surfaces 126, 128 provide a friction fit within the femur 112 against respective adjacent surface structures.

Figure 9:
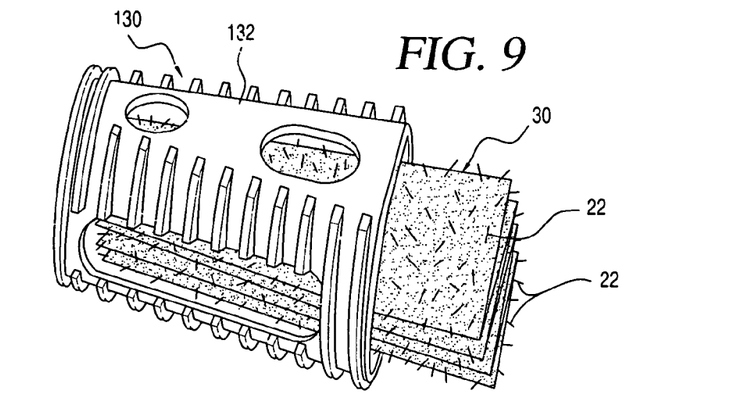
FIG. 9 is a schematic perspective view of a bone regenerative composition used in conjunction with a bone graft device.
Figure 10:
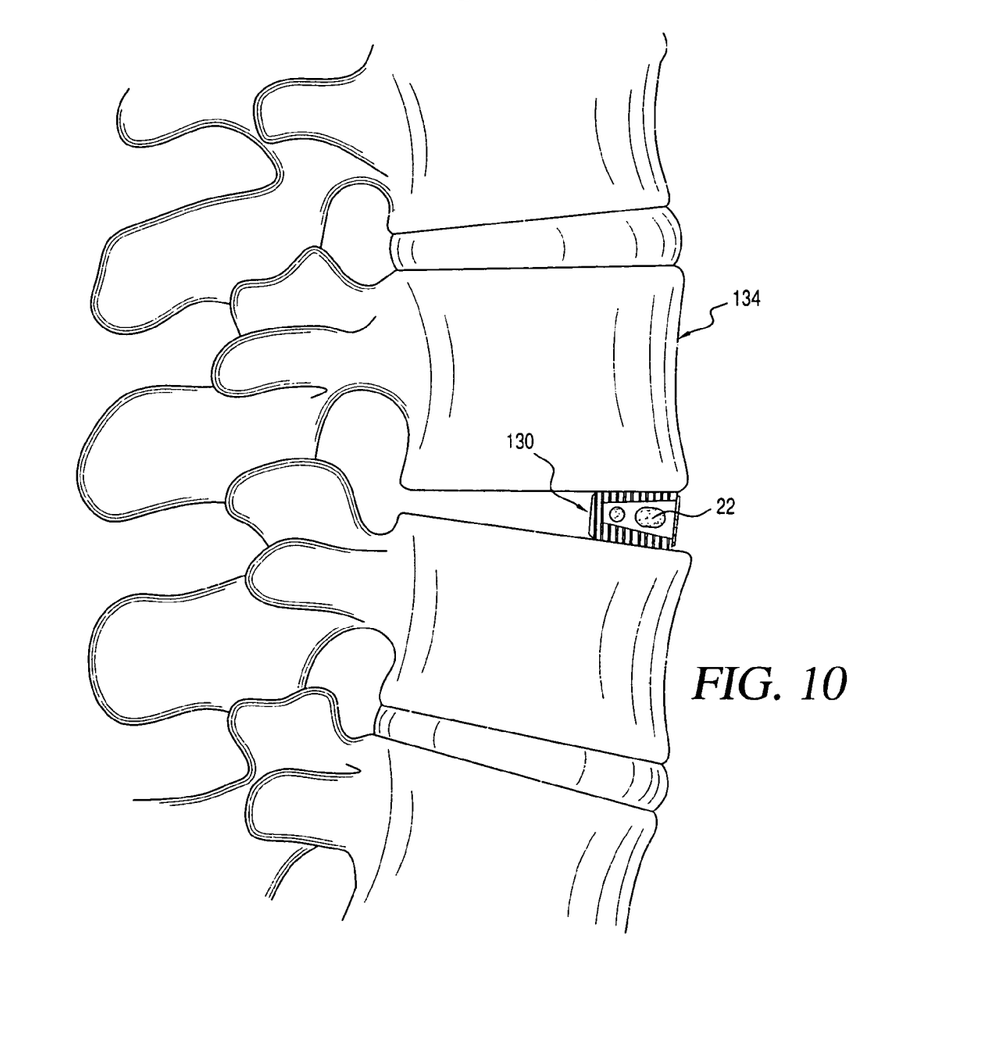
FIG. 10 is a schematic perspective view of the FIG. 9 device inserted within a spine.

FIGS. 9 to 10 illustrate another embodiment of the invention in which the resorbable osteoconductive matrix sheet 30 of the invention is used as a bone regeneration composition to form substantially three dimensional structures. In this embodiment, a conformable, resorbable sheet 30 is engineered from highly purified type I collagen. Resorbable means that the sheet 30 will undergo resorbtion, which is a process of absorbing again or dissolving and assimilating materials such as bone. This product can be cut with scissors to a desired shape and size. It is fully conformable when hydrated. The sheet can be rolled into a tube or used as a flat sheet. Or in the embodiment illustrated in FIGS. 9 and 10, the sheet 30 is folded to fit within a fusion cage 132.

FIGS. 9 and 10 show the bone regenerative composition 30 used in conjunction with an INFUSE® Bone Graft device 130 (Medtronic Sofamor Danek, Memphis, Tenn.) that includes a Bone Graft/LT-CAGE® Lumbar Tapered Fusion Device 132 (Medtronic Sofamor Danek, Memphis, Tenn.). The INFUSE® device 130 comprises two parts: (1) a genetically-engineered human protein (rhBMP-2) to stimulate bone healing, and (2) the absorbable collagen sponge (ACS) scaffold made from cow (bovine) collagen 30 that is soaked with the BMP. BMP can be bound to the ACS by soaking. Sufficient binding of BMP to ACS can be obtained by allowing a minimum of 15 minutes soaking time.

The INFUSE® device 130 can be used to help fuse vertebrae in the lower spine 134 to treat degenerative disc disease as shown in FIG. 10. The bristled surfaces of the ACS provide support against imposing anatomical tissue to assure uniform delivery of the BMP at the fusion site.

Other uses of the bone regenerative composition of the invention include oral/maxillofacial applications for maxillofacial bone repair; hemostats and wound dressings for oral surgeries; orthopedic/spine applications including bone and tendon repair; dermatological applications as collagen hemostats (fibrillar and sponge form) for general and trauma surgeries and wound care and as collagen wound dressings for general surgeries and chronic wound care; cardiovascular applications; as devices for the treatment of vascular diseases; in drug delivery technology for reduction of stenosis; as collagen-based coatings for treatment of aneurysms; and other applications.

The resorbable osteoconductive matrix enables a therapeutic physiological communication or migration of cells or fluids between host tissues and subsequent construct or composite of tissues, matrices, bone graft, bone graft substitutes, growth factors, peptides, pharmacological adjuncts, prostheses and implants. It serves a tissue-guided healing role that confines the therapeutic processes to an optimal location, range of motion, biomechanical role and kinematic function within the body. The resorbable osteoconductive matrix can act as a complete or partial barrier or channel to direct or target a physiological communication and transfer of cells or fluid media deemed beneficial to a medical outcome. The resorbable osteoconductive matrix has features that allow or enable or are responsive or sensitive to the influence of both internal and external stimuli such as active and passive electrical stimulation, photosensitivity, drug delivery depots or coatings or infiltration/inflation technologies and sensor technologies. The osteoconductive matrix sheet of the invention can provide enough inherent mechanical strength to withstand pressure from adjacent musculature without collapse. The nano-sized fibers provide an ACS with improved anatomic conformity and improved fit. Additionally, the nanofiber-containing structures allow for improved sorption over structures that include larger sized additives.

While preferred embodiments of the invention have been described, the present invention is capable of variation and modification and therefore should not be limited to the precise details of the examples. The invention includes changes and alterations that fall within the purview of the following claims.

What is claimed is:

1. A bone regenerative composition, comprising a resorbable osteoconductive matrix having a structure and a plurality of sides, each side having a surface, the resorbable osteoconductive matrix being in a sheet form; and a multiplicity of substantially rigid nanofibers uniformly dispersed within the structure of the matrix to impart structural integrity and with nanofiber ends projecting out of each surface of the matrix to provide differential load bearing surface bristles, wherein the nanofiber ends project out at least 10 nm from each surface of the matrix.

2. The bone regenerative composition of claim 1, wherein at least one of the nanofibers is a nanowire, nanowhisker, semi-conducting nanofiber, carbon nanotube or composite nanotube.

3. The bone regenerative composition of claim 1, comprising ACS with a nanofiber density of 10 nanofiber per 100 micron$^3$ to 200 nanofibers per micron$^3$ ACS volume.

4. The bone regenerative composition of claim 1, wherein the resorbable osteoconductive matrix is ACS comprising dispersed nanofiber ends elevated at least 100 nm above each ACS surface.

5. The bone regenerative composition of claim 1, wherein the matrix comprises pores that have a size range of from 10 µm to 500 µm.

6. The bone regenerative composition of claim 1, comprising ACS with a nanofiber density of 1 nanofiber per 10 micron$^3$ to 100 nanofibers per micron$^3$ ACS volume.

7. The bone regenerative composition of claim 1, comprising ACS with a nanofiber density of 1 nanofiber per 25 micron$^3$ to 75 nanofibers per micron$^3$ ACS volume.

8. The bone regenerative composition of claim 1, further comprising a supported interposed osteoinductive material.

9. An implant comprising:
a resorbable osteoconductive matrix sheet formed in a shape for implanting into a tissue area in need of regeneration, the resorbable osteoconductive matrix sheet comprising a plurality of sides, each side having a surface; and
a supported interposed osteoinductive material;
wherein the resorbable osteoconductive matrix sheet comprises substantially rigid nanofibers uniformly dispersed within a structure of the matrix sheet to impart structural integrity with nanofiber ends projecting out of each surface of the matrix sheet to provide differential load bearing bristled surfaces, wherein the nanofiber ends project out at least 10 nm from each surface of the matrix sheet.

10. The implant of claim 9, comprising a femoral stem member for use in an artificial hip implant assembly, having: a shaft portion with a proximal end and a distal end, the distal end being shaped for insertion into the axial bore of a patient's femur, and the proximal end including a ball-shaped surface for insertion into a receiving cup disposed in an acetabular recess in a patient's pelvis, and wherein the resorbable osteoconductive matrix comprises a multicellular matrix sheet with dispersed nanofiber and bristled surfaces that is wrapped around the shaft portion to provide differential load bearing and friction fitting bristled surfaces against adjacent structures in the area of the implant.

11. The implant of claim 9, comprising a tibial implant having a stem adapted to be fitted into a tibial canal; a load bearing component with longitudinal axis and adapted to approximate the size and shape of a tibial plateau; and an intermediate stem extension for operatively connecting the stem to the load bearing component; and wherein the resorbable osteoconductive matrix comprises a multicellular matrix sheet with dispersed nanofiber and bristled surfaces that is wrapped around the stern to provide differential load bearing and friction fitting bristled surfaces against adjacent structures in the area of the implant.

12. The implant of claim 9, comprising a femoral implant having a stem adapted to be fitted into a femoral canal; a load bearing component having a longitudinal axis and adapted to approximate the size and shape of condyles of a femur; and an intermediate stem extension for operatively connecting the stem to the load bearing component; and wherein the resorbable osteoconductive matrix comprises a multicellular matrix sheet with dispersed nanofiber and bristled surfaces that is wrapped around the shaft portion to provide differential load bearing and friction fitting bristled surfaces against adjacent structures in the area of the implant.

13. A kit comprising:
an implant; and
a resorbable osteoconductive matrix sheet formed in a shape for implanting with the implant into a tissue area in need of regeneration, the resorbable osteoconductive matrix sheet comprising a plurality of sides, each side having a surface; and a supported interposed osteoinductive material; wherein the resorbable osteoconductive matrix sheet comprises substantially rigid nanofibers uniformly dispersed within a structure of the matrix sheet to impart structural integrity and with nanofiber ends projecting out of each surface of the matrix sheet to provide differential load bearing bristled surfaces to the matrix sheet surface, wherein the nanofiber ends project out at least 10 nm from each surface of the resorbable osteoconductive matrix sheet.

\* \* \* \* \*